(12) United States Patent
Taylor et al.

(10) Patent No.: US 10,932,764 B2
(45) Date of Patent: *Mar. 2, 2021

(54) SURGICAL TISSUE RETRIEVAL INSTRUMENT AND METHOD OF USE OF A SURGICAL TISSUE RETRIEVAL INSTRUMENT

(71) Applicant: Conmed Corporation, Utica, NY (US)

(72) Inventors: James Taylor, Bartlett, IL (US); Robert H. Thrun, Bloomingdale, IL (US)

(73) Assignee: Conmed Corporation, Utica, NY (US)

( * ) Notice: Subject to any disclaimer, the term of this patent is extended or adjusted under 35 U.S.C. 154(b) by 229 days.

This patent is subject to a terminal disclaimer.

(21) Appl. No.: 16/128,964

(22) Filed: Sep. 12, 2018

(65) Prior Publication Data

US 2019/0008496 A1 Jan. 10, 2019

Related U.S. Application Data

(63) Continuation-in-part of application No. 15/135,421, filed on Apr. 21, 2016, now Pat. No. 10,098,619, which is a continuation-in-part of application No. 14/526,249, filed on Oct. 28, 2014, now Pat. No. 9,414,817, which is a continuation of application No. 13/309,854, filed on Dec. 2, 2011, now Pat. No. 8,870,894, which is a continuation of application No. 12/079,172, filed on Mar. 24, 2008, now Pat. No. 8,075,567.

(60) Provisional application No. 60/919,386, filed on Mar. 22, 2007.

(51) Int. Cl.
*A61B 17/00* (2006.01)
*A61B 17/28* (2006.01)
*A61B 17/32* (2006.01)

(52) U.S. Cl.
CPC ...... *A61B 17/00234* (2013.01); *A61B 17/282* (2013.01); *A61B 2017/00287* (2013.01); *A61B 2017/00473* (2013.01); *A61B 2017/320008* (2013.01)

(58) Field of Classification Search
CPC .... A61B 2017/00287; A61B 17/00234; A61B 17/221; A61B 2017/12054
See application file for complete search history.

(56) References Cited

U.S. PATENT DOCUMENTS

2004/0097963 A1* 5/2004 Seddon ............... A61B 17/221
606/127
2007/0088370 A1* 4/2007 Kahle ............. A61B 17/00234
606/114
2007/0135781 A1* 6/2007 Hart ................ A61B 17/00234
604/327

* cited by examiner

Primary Examiner — Katherine M Shi
(74) Attorney, Agent, or Firm — Bond, Schoeneck & King, PLLC; Frederick J. M. Price

(57) ABSTRACT

A surgical tissue retrieval instrument has a collapsible pouch at the distal end of an elongated pusher rod that is introduced into a patient through a cannula. The instrument includes a two jaw fork that forms a loop when in an unconstrained configuration and that supports the pouch. Deployment and operation of the fork and the pouch are controlled by a securing mechanism. The two jaws and the securing mechanism are slid in a hem surrounding the opening of the pouch when the device is assembled.

5 Claims, 16 Drawing Sheets

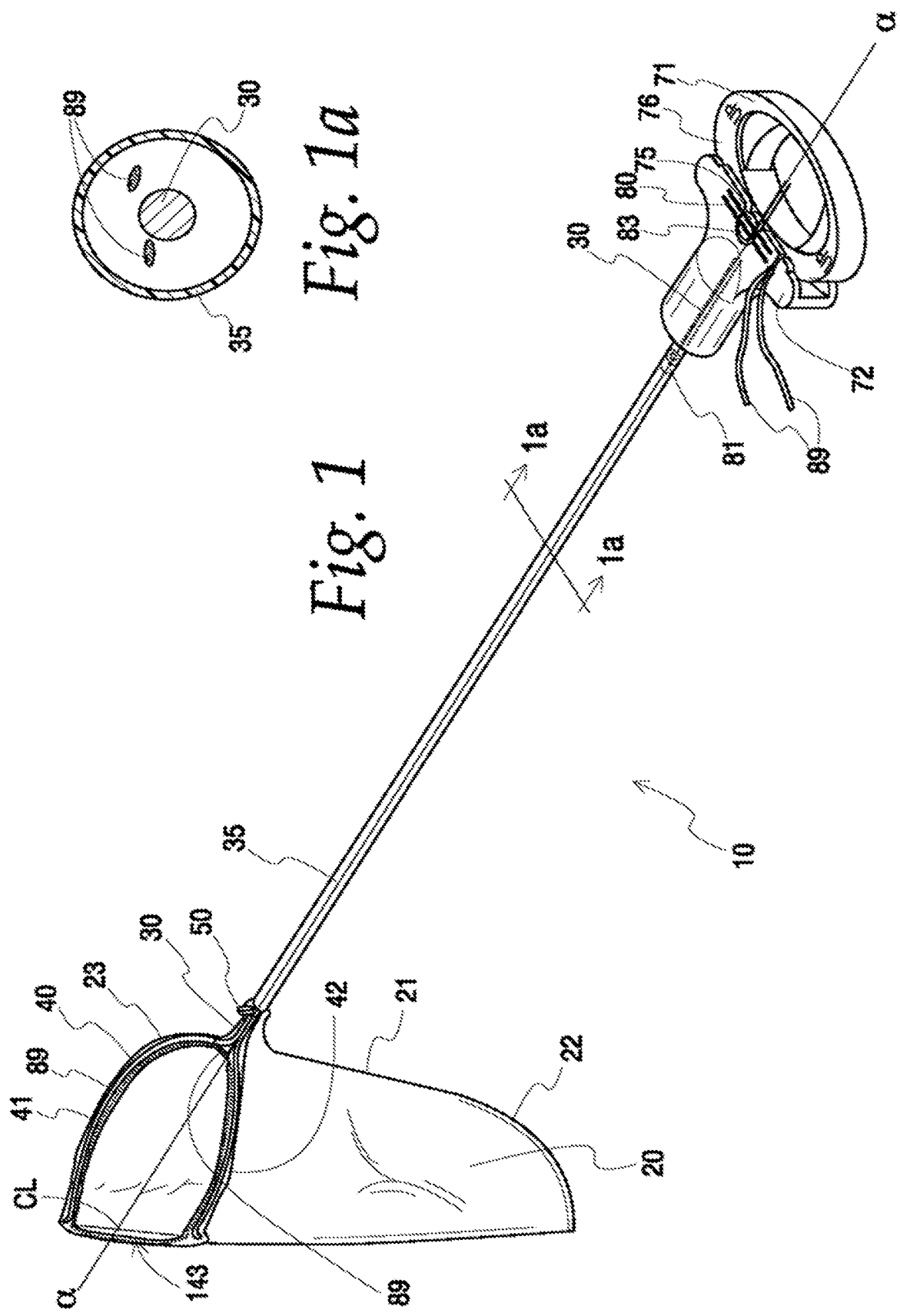

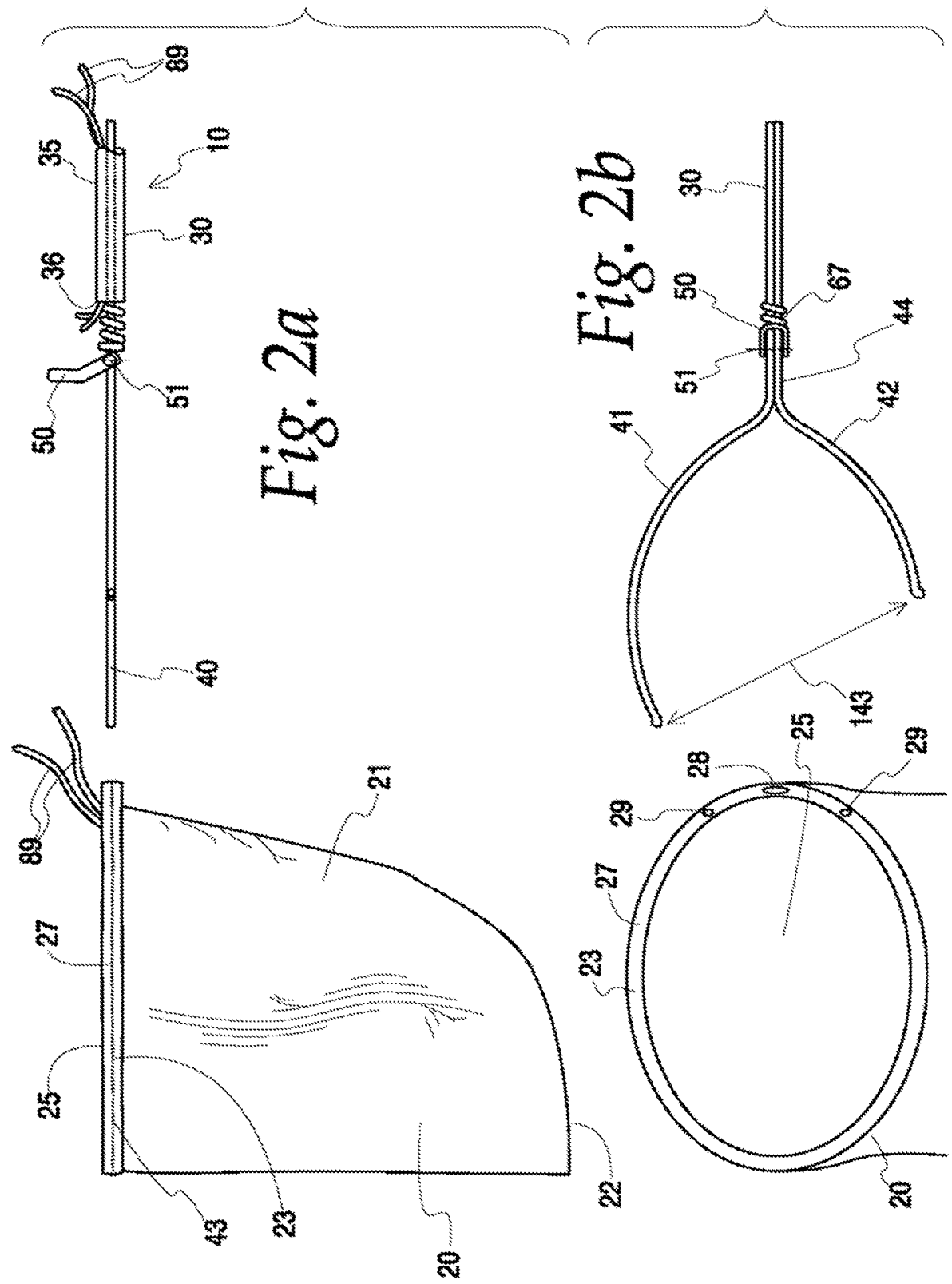

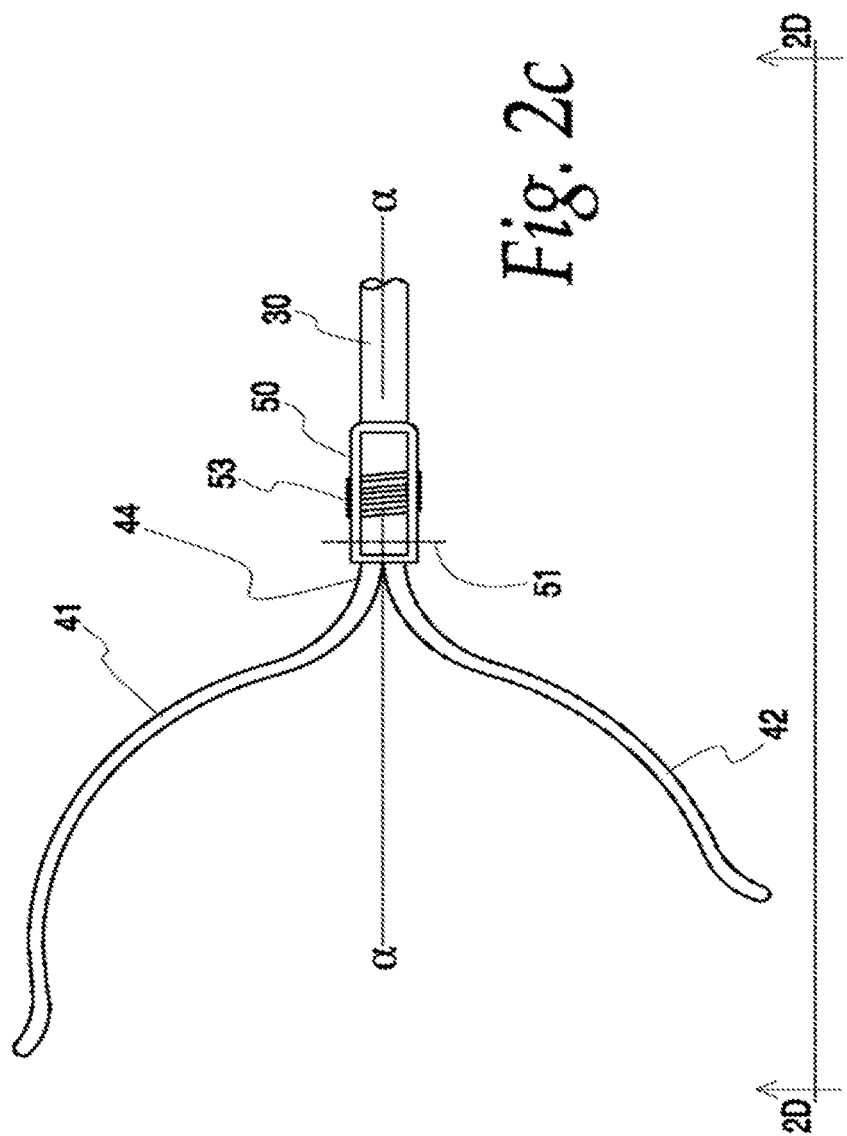
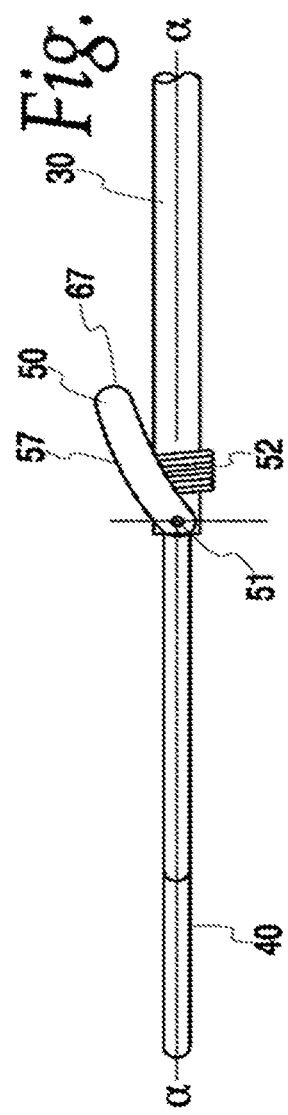

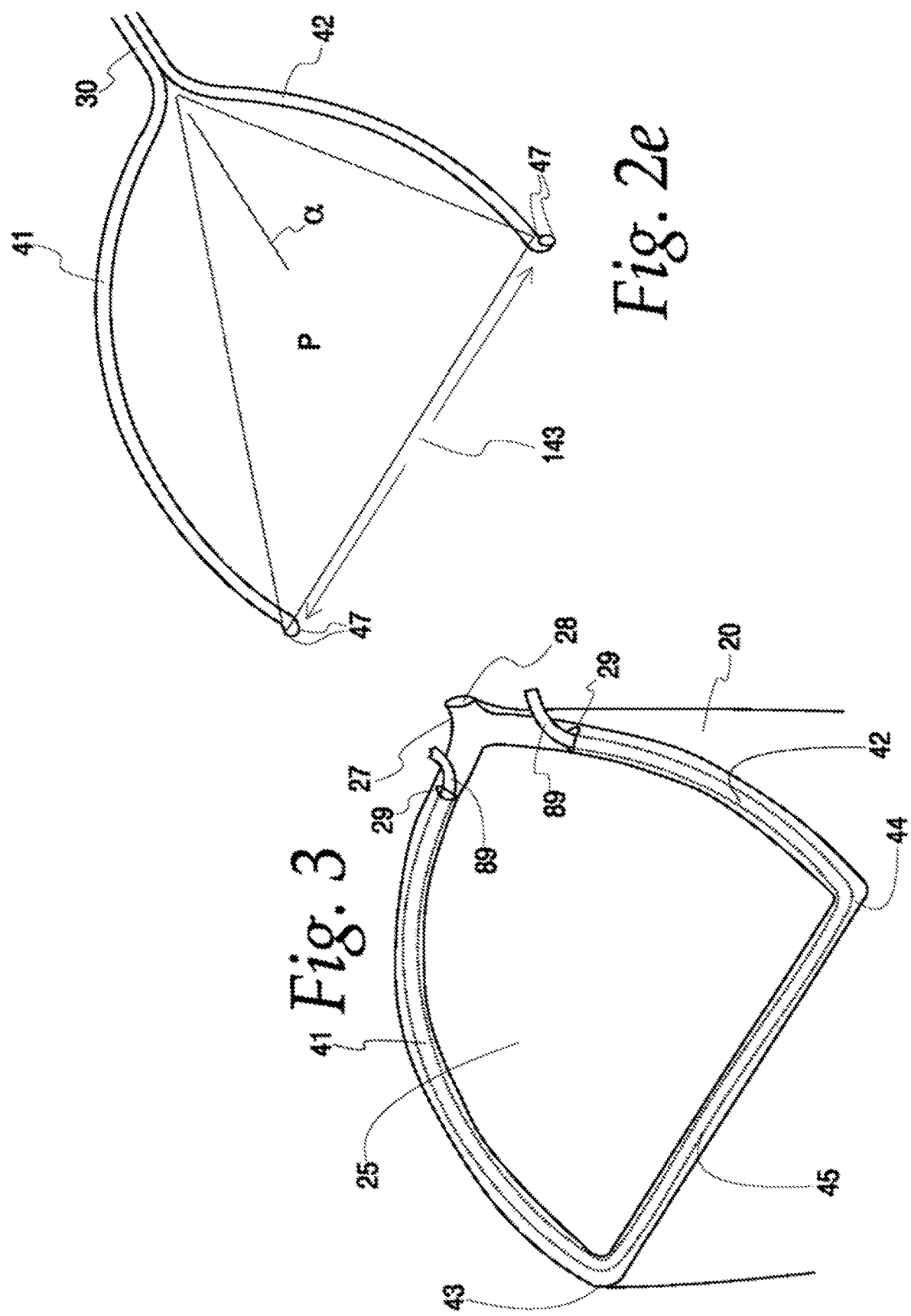

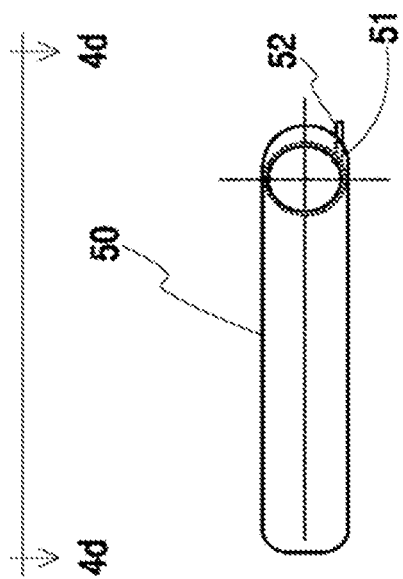
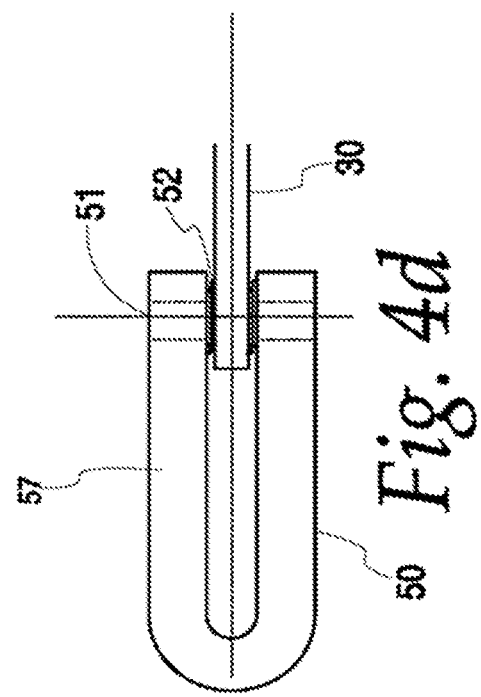

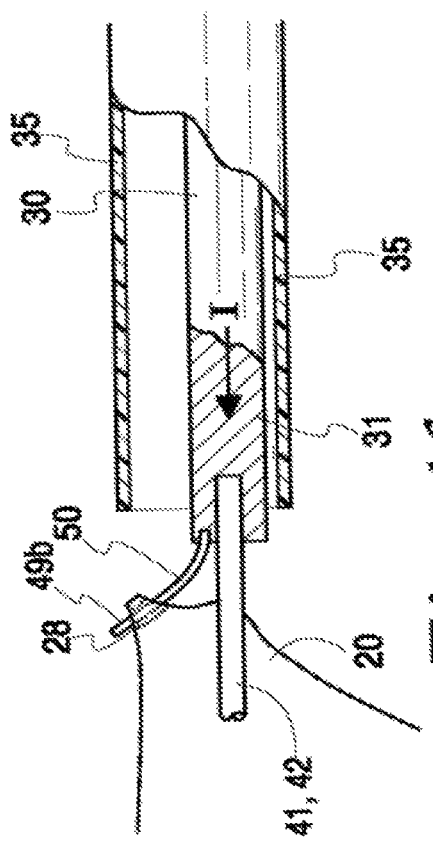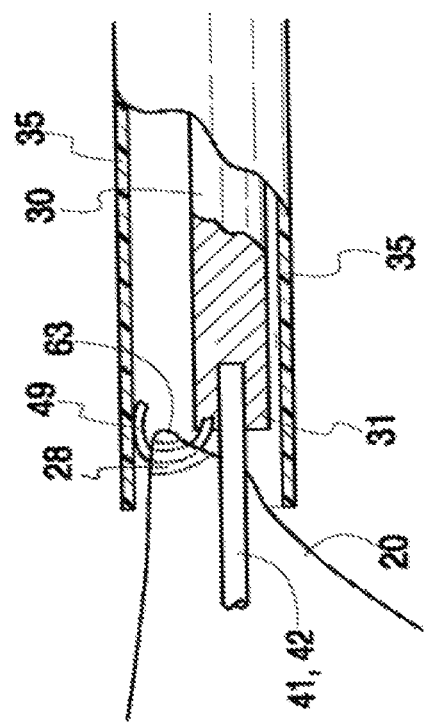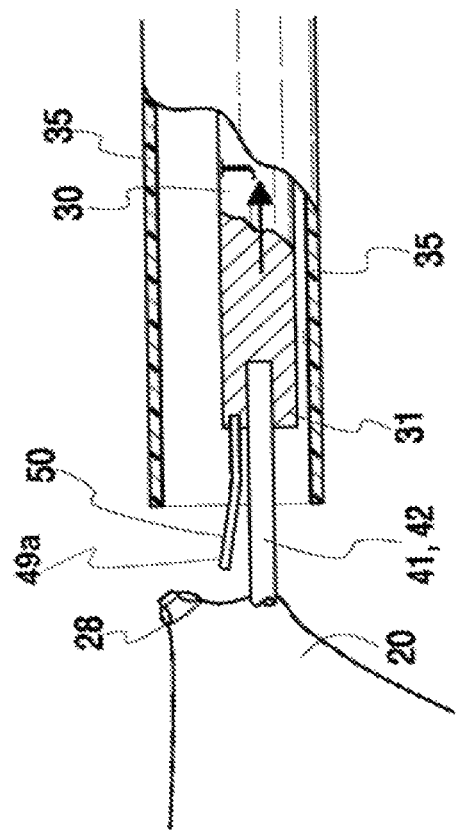

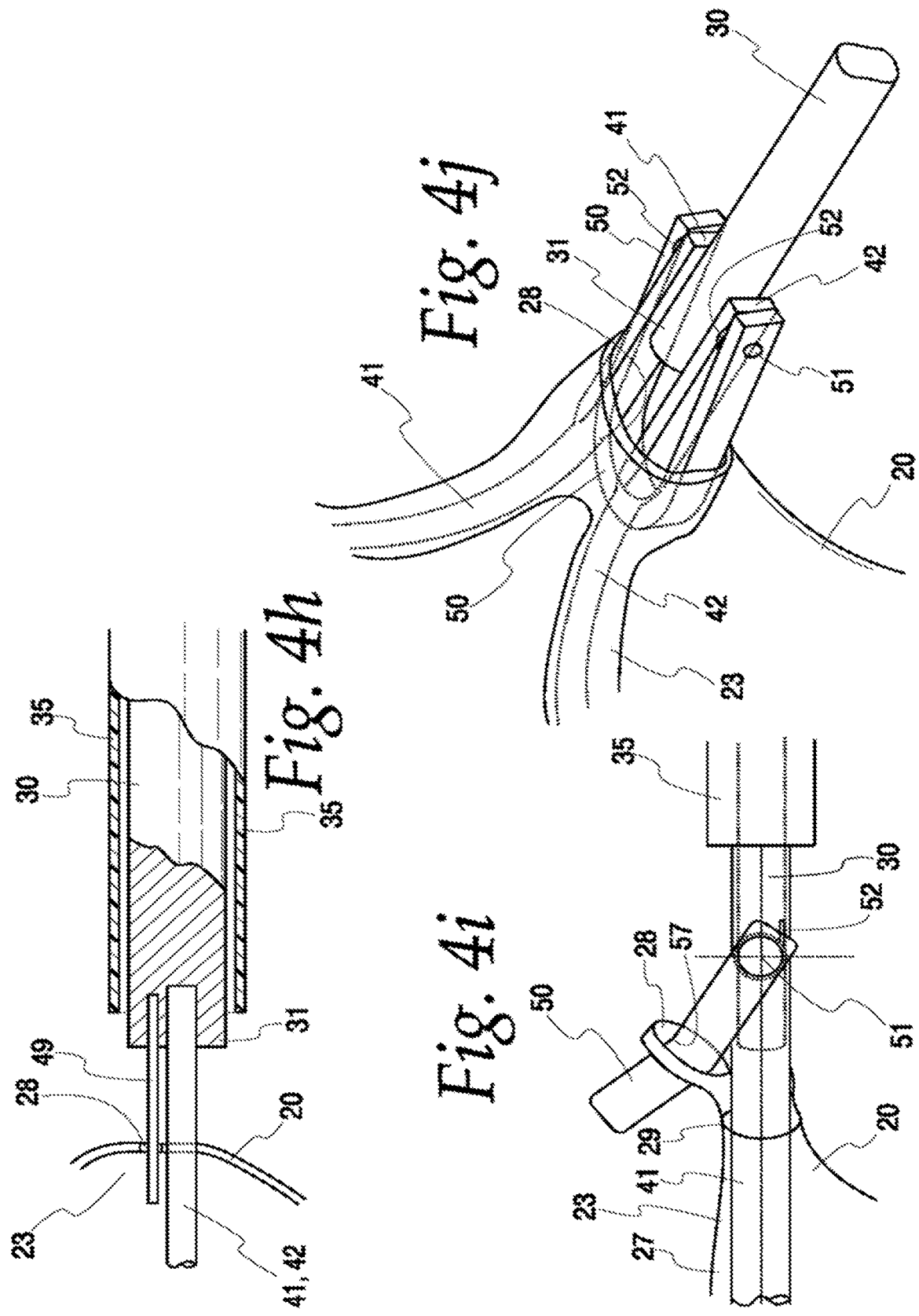

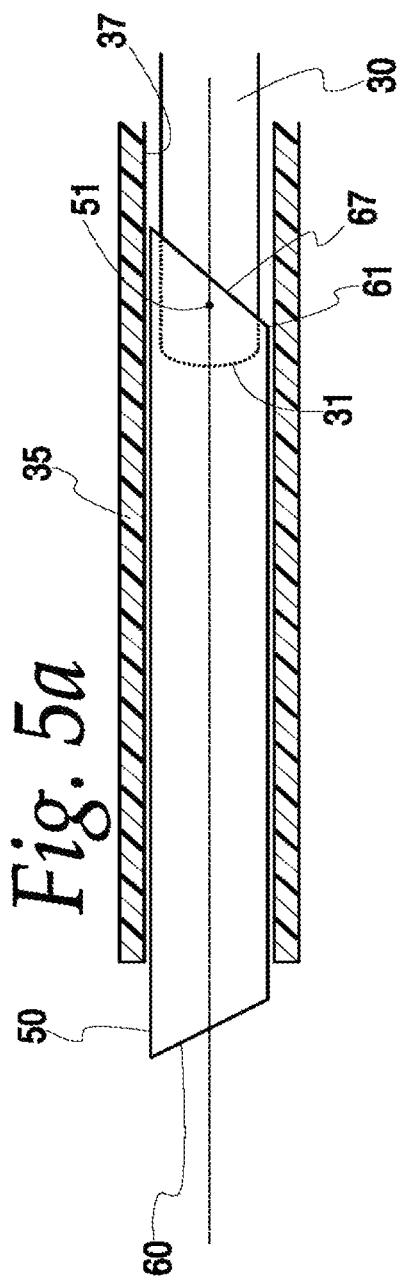
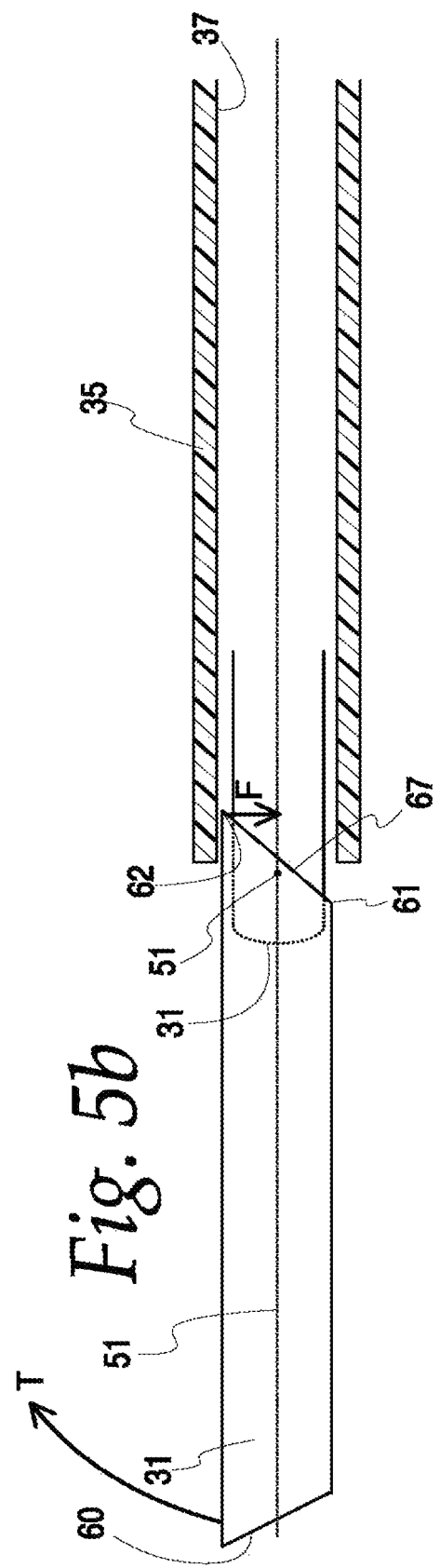

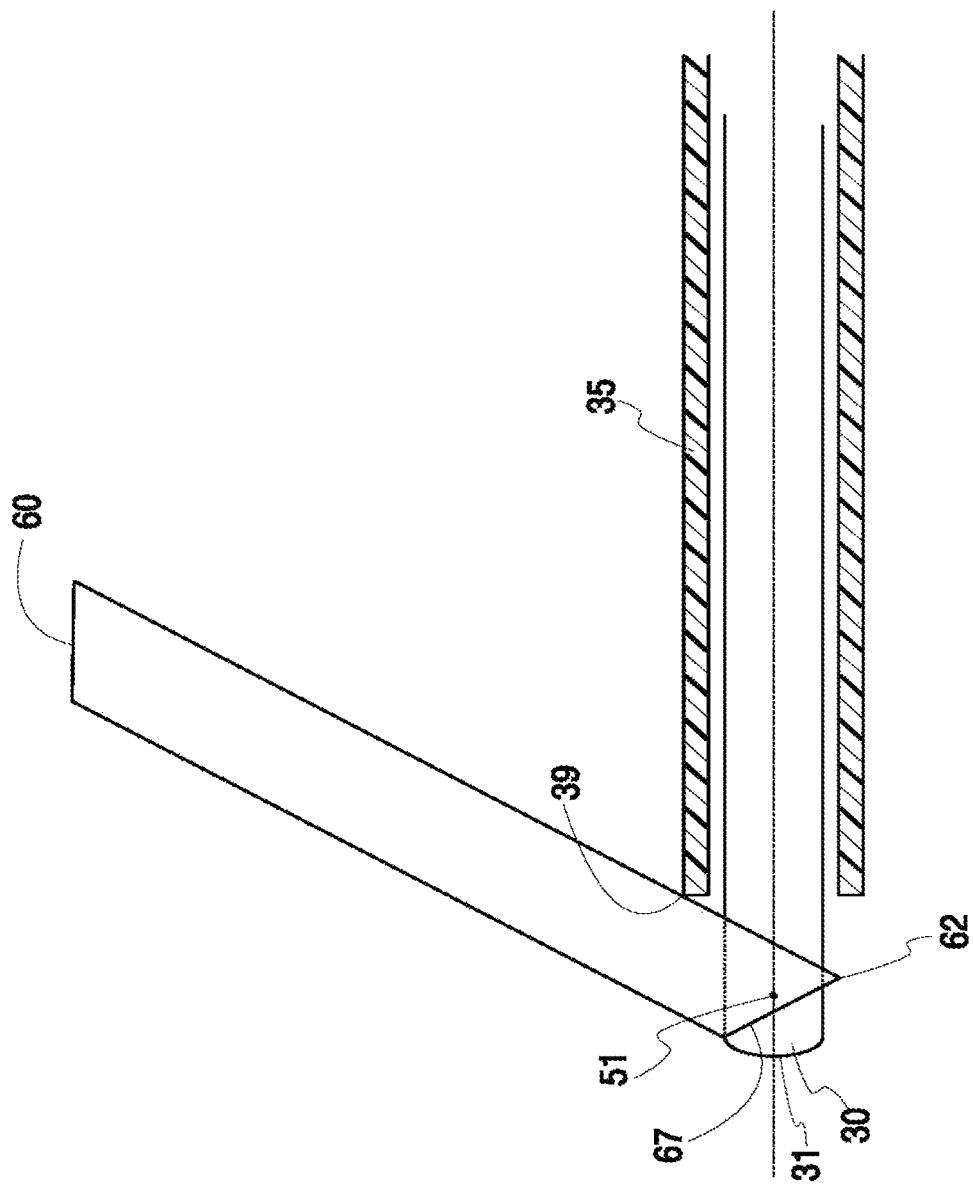

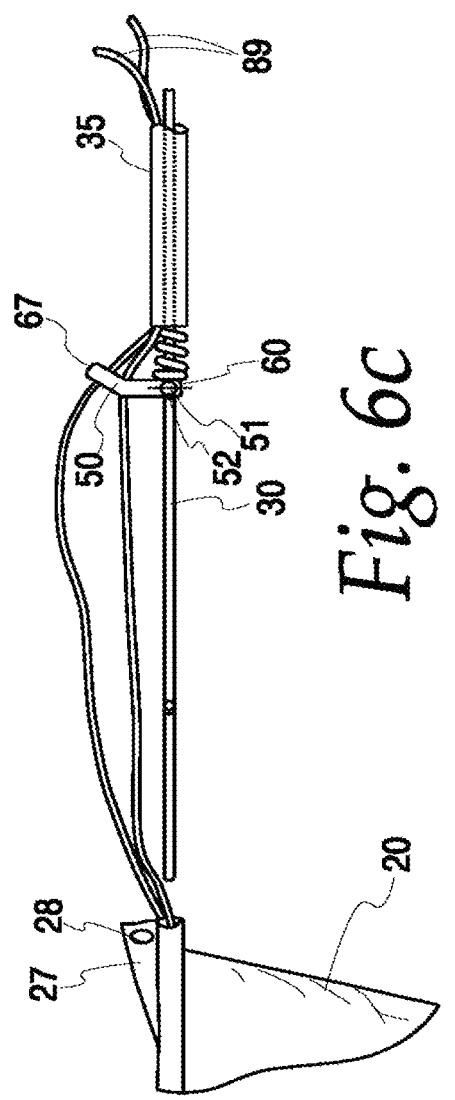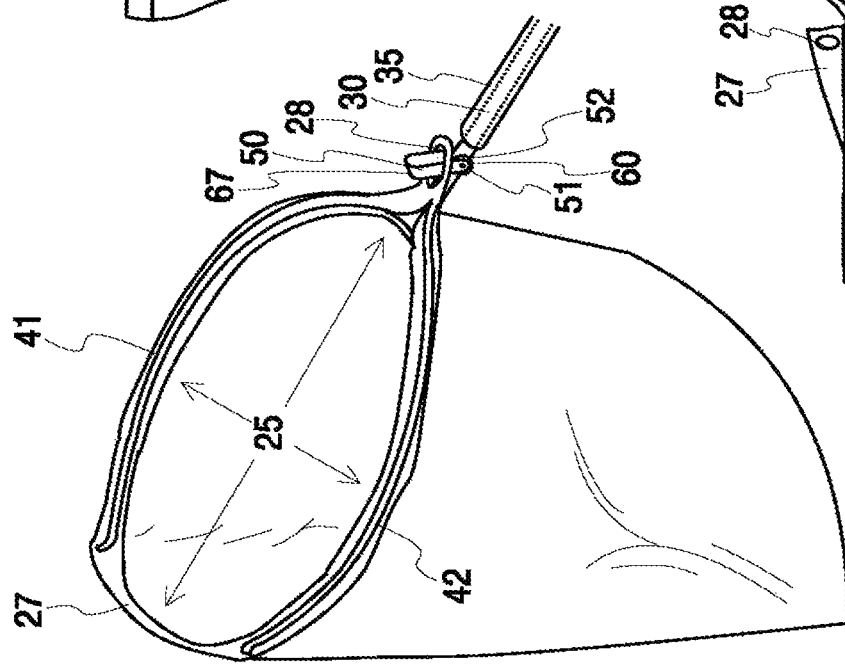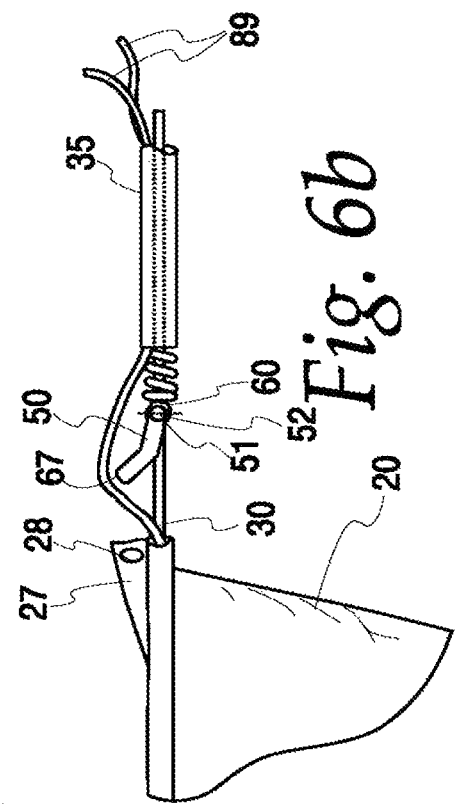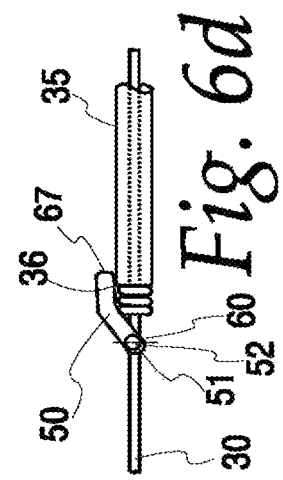

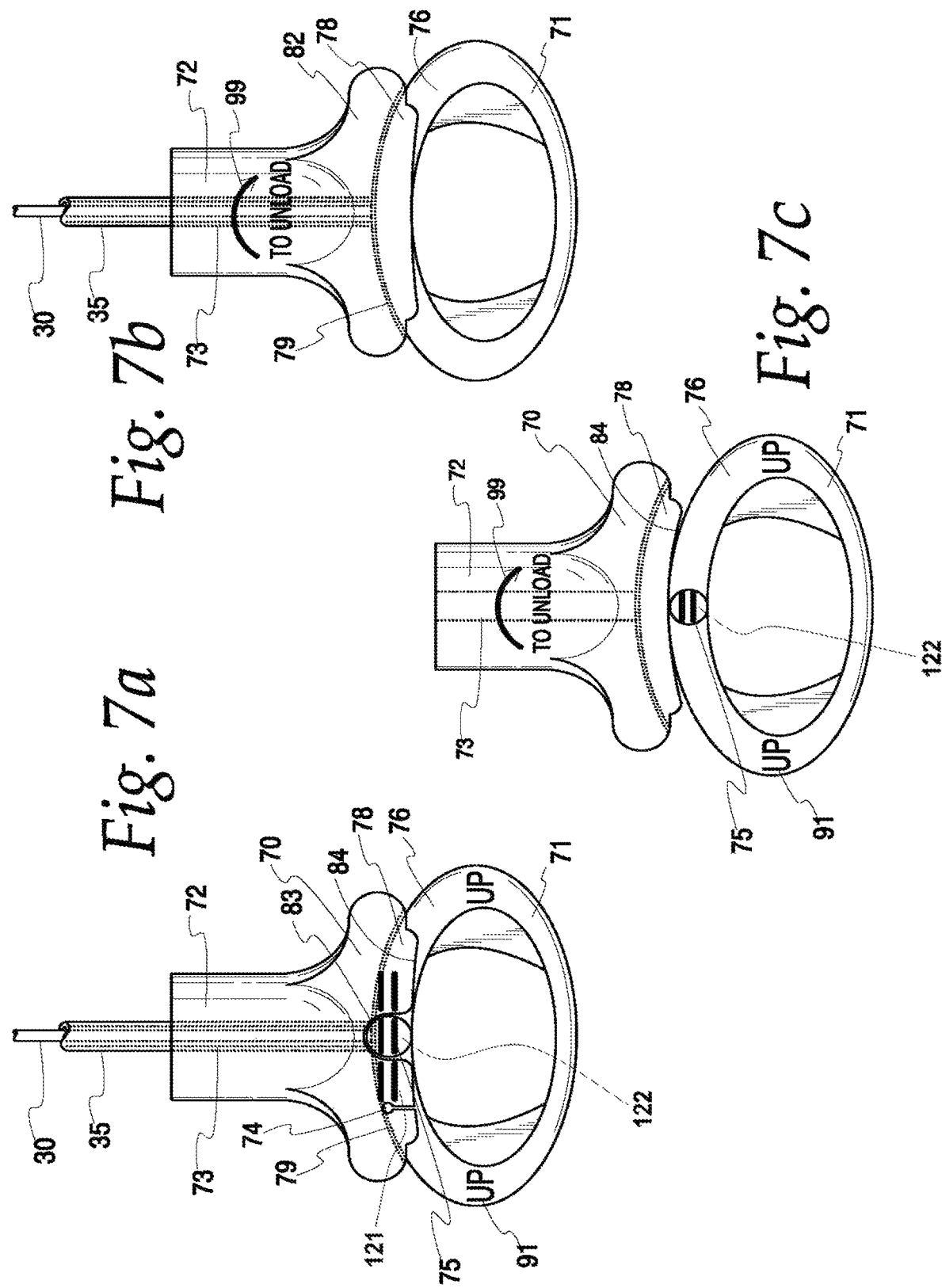

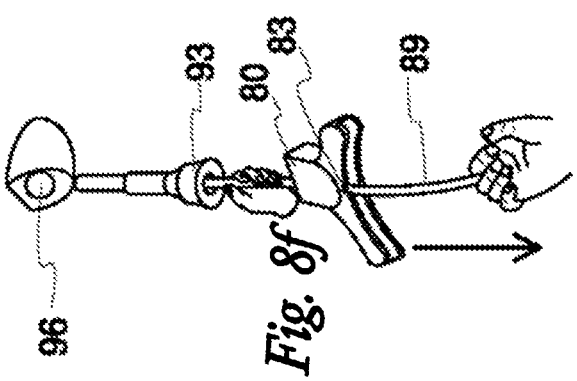
Fig. 8f
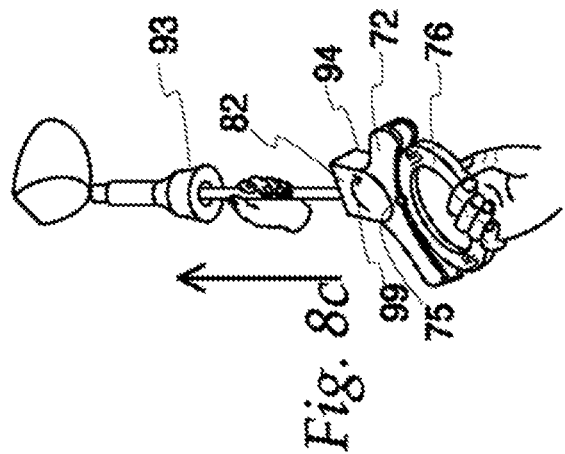
Fig. 8d
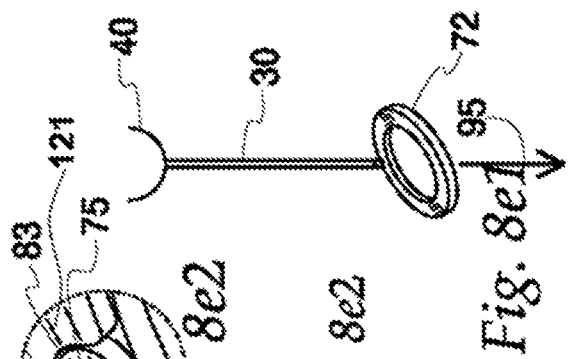
Fig. 8e1
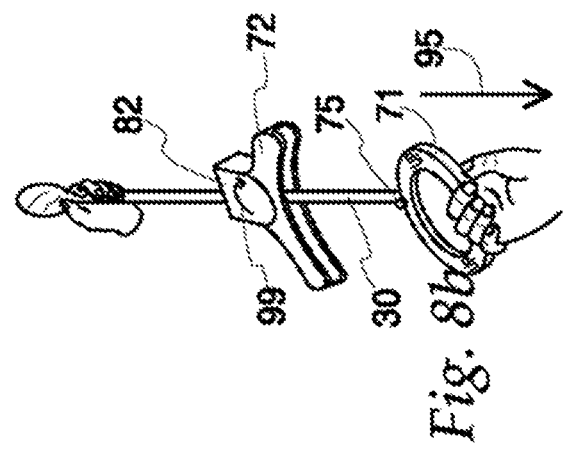
Fig. 8b
Fig. 8e2
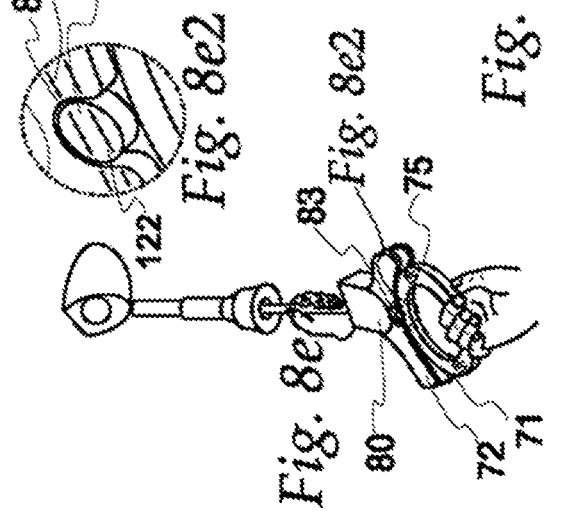
Fig. 8e2
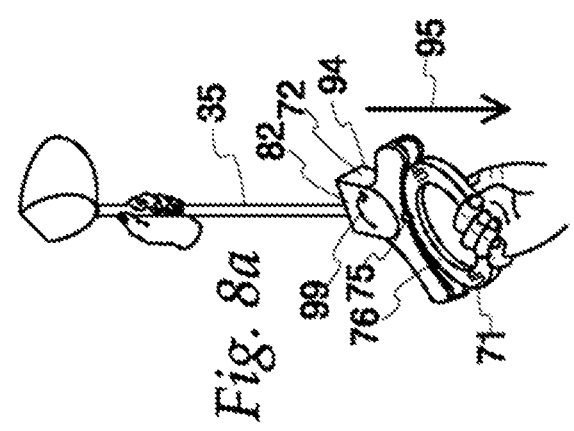
Fig. 8a
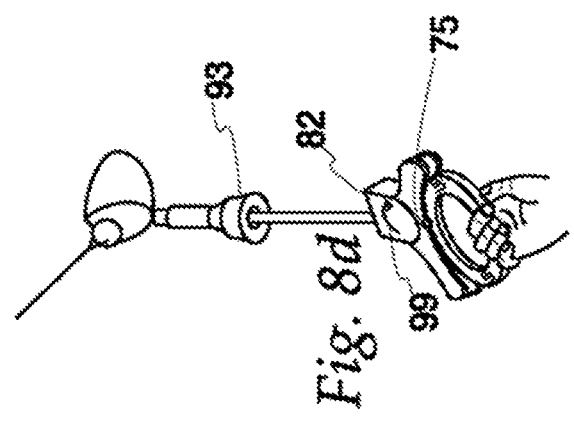
Fig. 8d

SURGICAL TISSUE RETRIEVAL INSTRUMENT AND METHOD OF USE OF A SURGICAL TISSUE RETRIEVAL INSTRUMENT

CROSS-REFERENCE TO RELATED APPLICATION

This utility application is a continuation in part of U.S. application Ser. No. 15/135,421 filed on Apr. 21, 2016, which in turn is a continuation in part of U.S. application Ser. No. 14/526,249, filed on Oct. 28, 2014, currently patented as U.S. Pat. No. 9,414,817, issued on Aug. 16, 2016, which in turn was a continuation of and claimed the benefit of U.S. Utility application Ser. No. 13/309,854, filed on Dec. 2, 2011, currently patented as U.S. Pat. No. 8,870,894 issued on Oct. 28, 2014, which in turn was a continuation of and claimed the benefit of U.S. Utility application Ser. No. 12/079,172, filed on Mar. 24, 2008, currently patented as U.S. Pat. No. 8,075,567 issued on Dec. 13, 2011, which in turn claimed priority benefit to U.S. Provisional Application No. 60/919,386 filed Mar. 22, 2007, currently expired. The contents of each application are hereby incorporated by reference.

BACKGROUND OF THE INVENTION

Field of the Invention

This invention relates to the field of surgical instruments for retrieving internal body tissue and, more particularly, to a surgical instrument used in endoscopic surgery for retrieving internal body tissue with an endoscopic pouch.

Description of the Related Art

Tissue retrieval devices have been developed for use in endoscopic surgery to remove tissue from a patient's body. Typically these devices comprise a specimen-collecting pouch placed at the distal end of a pusher rod. The pusher rod is inserted into the patient's body via a tiny insertion and the pouch is deployed once it is near the surgical site. Gaining close proximity to the tissue to be removed, placing the tissue in the pouch, closing the pouch, and removing the now-filled pouch from the body are the main steps to be performed with the device.

Pouches used with tissue retrieval devices often employ a means for closing the pouch to prevent spillage of tissue or fluids into the patient's body. Typical closure means include a drawstring or a wire loop.

In many state of the art devices, the mouth of the pouch does not allow for easy collection of the sample and/or removal of the pouch from the patient's body. This is because of problems associated with the slipknot often used to initially close the pouch. For example, in some prior art devices, once the pouch is closed it cannot be reopened until the pouch is removed from the patient.

A surgical retrieval device with a drawstring for closing the pouch is disclosed by Clayman et al., U.S. Pat. No. 5,037,379. The drawstring is used to close the bag closed and pull the bag from the body cavity through a tube.

Kindberg et al., U.S. Pat. No. 5,143,082, discloses a surgical device for enclosing a body organ or tissue and which includes a strand extending through a tube and formed into a noose about the open end of a surgical bag.

Wetter et al., U.S. Pat. No. 5,190,555, discloses another endoscopic tissue retrieval device that includes a drawstring used for closing and opening a funnel-shaped bag.

U.S. Pat. Nos. 5,465,731 and 5,647,372 disclose yet another endoscopic tissue retrieval comprising a pouch supported by a closed metal loop. The bag is ripped away from the metal loop during the drawstring closure along a perforated line circumscribing the mouth of the pouch.

The aforementioned patents and device are not admitted to be prior art by their mention in this Background section.

Many state-of-the-art pouches fail during their removal from the patient. This is because a great deal of force is applied to a filled bag as a surgeon attempts to pull it through the typically tiny laparoscopic surgical incision made in the skin and muscle layers of the patient.

Separately, bags often come into contact with sharp surgical instruments and rip as a result.

A need exists in the art for a reliable tissue retrieval device comprising a sturdy bag with a large mouth that is securely attached to its support but that can be released from the support without having to close the mouth of the bag. Such a device should also allow full access to the retrieval pouch prior to insertion into the patient so as afford in situ pretreatment of the bag. Furthermore, the device should provide a means for preventing accidental deployment or closure of the pouch as well as accidental removal of the pouch from its support during collection of tissue. The device should also provide a means to scrape tissue from adjacent adhering structures for more efficient tissue extraction from the body.

BRIEF SUMMARY OF THE INVENTION

An object of this invention is to provide a tissue retrieval device for use in endoscopic surgery that overcomes many of the disadvantages in the prior art.

Another object of the invention is to provide a surgical tissue retrieval device comprising a pouch which is securely but removably attached to a support. A feature of this invention is a means for facilitating repeated deployment, opening, and closing of the pouch while the pouch is still confined inside the patient. An advantage of this invention is that it allows quick release of the pouch from its support without having to lock or close the mouth of the pouch. Another advantage of this invention is that it allows a surgeon to serially collect samples while the device remains inside the body and to securely close and reopen the pouch.

Yet another object of the invention is to provide an endoscopic collection device that enables a surgeon to remove tissue and treat unremoved tissue. A feature of an embodiment of this invention is a pouch propped open by two elongated substrates of unequal length that are slidably received by the pouch, and held in position by the action of a controlling toggle. An advantage of this invention is that a portion of the mouth of the pouch remains taut while the pouch is open and can be used as a straight scraping edge. Another advantage of this invention is that it allows the pouch to be rotated or moved transversely while the pouch is either closed or opened. This allows a surgeon to retrieve tissue that tends to adhere to nearby anatomical structures such as organs, mesentery, and surrounding structures. Another advantage of this invention is that it allows a surgeon to retrieve tissue by providing a means for positioning the tissue-collecting portion of the device in regions located generally perpendicular to or lateral from the longitudinal axis of the device.

A further object of the present invention is to provide a tissue retrieval tool for use in laparoscopic procedures. A feature of the device is a means for reversibly deploying the tissue removal bag and reversibly opening and closing the bag both inside and outside the body. An advantage of the invention is that a deployed bag outside the body allows medical personnel to manipulate the bag and to pretreat the bag prior to inserting the bag into its delivery sleeve in preparation for entry into the patient. Another advantage of the invention is that it allows a bag, once deployed inside the body to be repeatedly closed and reopened inside the body, thereby enabling a surgeon to collect tissue while preventing any spillage thereof during varying, protracted harvesting procedures conducted inside the body.

In brief, this invention provides a surgical device for retrieving internal body tissue during laparoscopic and other surgical procedures, the device comprising a sleeve having a proximal end and a distal end, said distal end adapted for insertion in a cannula, a rod in slidable and rotatable communication with said sleeve, said rod having a distal end supporting a toggle and laterally biased jaws and a proximal end comprising a handle to manipulate the rod, and a pouch in slidable communication with the jaws and toggle, wherein the toggle facilitates simultaneous detachment of the pouch from the jaws and the rod.

The invention also provides a device for removing tissue from a patient's body, the device comprising: a sleeve having a proximal end and a distal end, said distal end adapted for insertion in a cannula; a pusher rod in slidable communication with said sleeve, the rod having a distal end terminating in laterally biased jaws and a proximal end terminating in a handle; a toggle pivotally mounted to the rod intermediate the proximal end and the distal end, such that the toggle swings from a first spring loaded position to a second resting position; and a pouch in slidable communication with the jaws and toggle; wherein the toggle allows disengagement of the pouch from the jaws when in the second resting position.

BRIEF DESCRIPTION OF THE DRAWINGS

The foregoing and other objects, aspects, and advantages of this invention will be better understood from the following detailed description of the preferred embodiments of the invention with reference to the drawing, in which:

FIG. 1 is an overall perspective view of an exemplary embodiment of a surgical device for retrieving internal body tissue, in accordance with features of the present invention;

FIG. 1a is a cross-sectional view of FIG. 1 along line 1a-1a;

FIG. 2a is a profile exploded view of an exemplary embodiment of a surgical device for retrieving internal body tissue, in accordance with features of the present invention;

FIG. 2b is a perspective exploded view of an exemplary embodiment of a surgical device for retrieving internal body tissue, in accordance with features of the present invention;

FIG. 2c is a plan exploded view of pouch supports of an exemplary embodiment of a surgical device for retrieving internal body tissue, in accordance with features of the present invention;

FIG. 2d is a profile view of FIG. 2c taken along line 2d-2d.

FIG. 2e is a detail view of a pouch support for a surgical device for retrieving internal body tissue, in accordance with features of the present invention;

FIG. 3 is a schematic plan view of a pouch opening for a surgical device for retrieving internal body tissue, in accordance with features of the present invention;

FIG. 4c is a profile view of an alternative embodiment of a toggle mechanism for a surgical device for retrieving internal body tissue, in accordance with features of the present invention;

FIG. 4d is a view of FIG. 4c taken along line 4d-4d;

FIG. 4e is a profile view of an alternative embodiment of a toggle mechanism for a surgical device for retrieving internal body tissue, with said mechanism engaged in the hem of the device's pouch, in accordance with features of the present invention;

FIG. 4f is a view of the toggle mechanism for a surgical device for retrieving internal body tissue depicted in FIG. 4e with said toggle about to be disengaged from the hem of the device's pouch, in accordance with features of the present invention;

FIG. 4g is a view of the toggle mechanism for a surgical device for retrieving internal body tissue depicted in FIG. 4e with said toggle disengaged from the hem of the device's pouch, in accordance with features of the present invention;

FIG. 4h is a detail view of an alternative embodiment of a toggle mechanism for a surgical device for retrieving internal body tissue depicted in FIG. 4e, in accordance with features of the present invention;

FIG. 4i is a detail view of a toggle mechanism and retrieval pouch for a surgical device for retrieving internal body tissue, in accordance with features of the present invention;

FIG. 4j is a detail view of an alternative embodiment of a toggle mechanism and retrieval pouch for a surgical device for retrieving internal body tissue, in accordance with features of the present invention;

FIG. 5a is a detailed view of an alternative embodiment of a toggle mechanism for a surgical device for retrieving internal body tissue, with said toggle fully contained in an introducer tube, in accordance with features of the present invention;

FIG. 5b is a detailed view of the toggle depicted in FIG. 5a with said toggle partially contained in an introducer tube, in accordance with features of the present invention;

FIG. 5c is a detailed view of the toggle depicted in FIG. 5a after said toggle has exited an introducer tube, in accordance with features of the present invention;

FIGS. 6a-6d is a sequence of detailed views of the relative orientation of a pouch and a toggle post for a surgical device for retrieving internal body tissue, in accordance with features of the present invention;

FIGS. 7a and 7b are, respectively, schematic front and back views of a handle assembly for a surgical device for retrieving internal body tissue, in accordance with features of the present invention;

FIG. 7c is a detailed view of the orientation of the handle assembly depicted in FIGS. 7a and 7b when the surgical device for retrieving internal body tissue is inserted in a patient, in accordance with features of the present invention;

FIGS. 8a-8f is a sequence of views illustrating the operation of a surgical device for retrieving internal body tissue; in accordance with features of the present invention;

FIG. 8e1 is a detailed view of the fork, pusher rod, and handle assembly comprised in the surgical device for retrieving internal body after this assembly is removed from a patient, in accordance with features of the present invention;

FIG. 8e2 is a detailed view of the relative handle and the handle housing orientation depicted in FIG. 8e for the surgical device for retrieving internal body when this device is removed from a patient, in accordance with features of the present invention;

DETAILED DESCRIPTION OF THE INVENTION

Figure 4A:
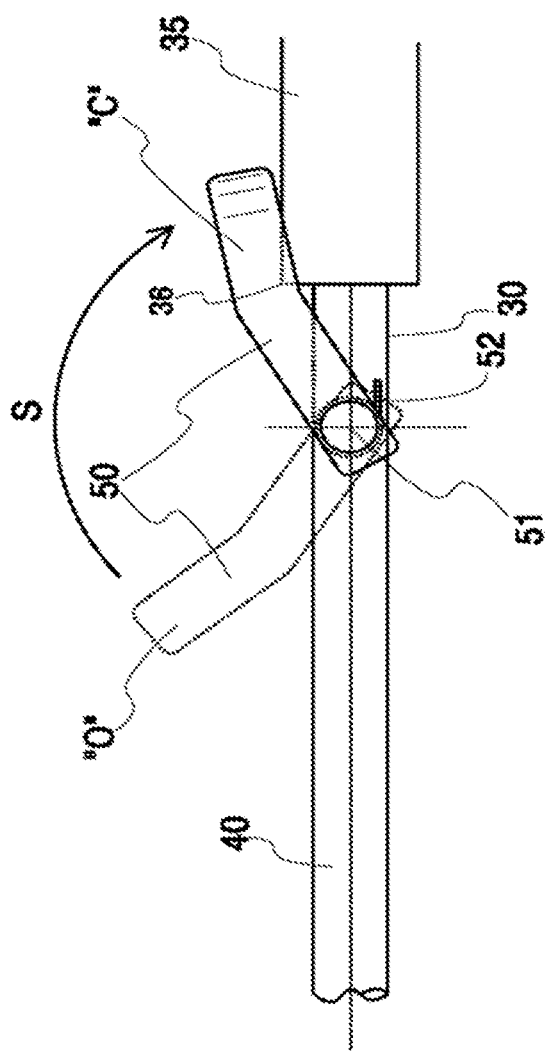
FIG. 4a is a detailed profile view of a toggle mechanism for a surgical device for retrieving internal body tissue, in accordance with features of the present invention.

The present invention provides a surgical tissue retrieval device for use in endoscopic surgery which overcomes disadvantages in the prior art. The device comprises a collapsible pouch defining a mouth, the mouth defined by a periphery which removably receives a plurality of elongated support jaws; and a toggle mechanism serving as a means for controlling the deployment, opening, and closing of the support jaws, and, therefore, the opening and closing of the mouth of the pouch.

The present invention also provides a device for removing tissue from a patient's body comprising a sleeve having a proximal end and a distal end, with said distal end adapted for insertion into a cannula; a rod in slidable and rotatable communication with said sleeve, the rod having a distal end terminating in a plurality of laterally biased jaws. A toggle is also positioned on the rod intermediate the jaws and proximal the end. A pouch is in slidable communication with the jaws and the toggle, wherein the toggle facilitates loading of the pouch during collection of tissue and detachment of the pouch from the jaws when this collection is terminated.

FIG. 1 is an overall perspective view of an exemplary embodiment of the invented device 10. The device facilitates retrieval of internal body tissue through a sleeve (i.e. an Introducer) 35 inserted into the body wall of a patient through a cannula (not shown). The surgical device further comprises an elongated substrate 30 such as pusher rod. The rod 30 is terminated by a plurality 40 of elongated jaws 41, 42 which when fully deployed in a spring biased position and viewed together resembles a circle. The pusher rod 30 is slidably received by the introducer 35. A proximal end of the rod terminates into a handle assembly comprising a handle 71 in slidable communication with a handle housing 72 containing a gasket 81 positioned through which the pusher rod 30 is slid through. The gasket is in frictional contact with both the rod and an inside surface of the introducer tube so as to prevent fluid communication (e.g. gas leakage) from the distal end to the proximal end of the sleeve 35. The top face 76 of the handle 71 comprises a protrusion 75 adapted to rest within a slot 83 on the top face 80 of the housing 72. (See detailed discussion infra of the handle assembly and its operation as related to FIGS. 7 and 8.)

In one embodiment, two elongated jaws are provided, with one jaw longer than the other such that the heretofore mentioned circular shape terminates in a cord line CL, so designated in FIG. 1. (Jaws of equal length can also be used.) These elongated jaws 41, 42 resemble a hanger or fork which slidably receives a collar (defining a mouth) of a collapsible pouch 20, such that the pouch, when so engaged, depends from the distal end of the pusher rod 30. The elongated jaws 41, 42 are spring biased such that when deployed (i.e. slid clear of the confines of the introducer 35), the jaws extend laterally (i.e., perpendicularly away from the longitudinal axis a of the device) to prop open the mouth of the pouch.

The cord line CL of the pouch serves as a straight edge, held taught by the biasing configuration of the deployed jaws, so as to provide a scraping function to the distal end of the device along that edge.

As can be seen in FIG. 2c, the device provides a means for repeatedly opening and closing the mouth of the pouch. Specifically, when the rod 30 is pulled toward the proximal end, the roots 44 of the jaws contact the distal end 31 of the introducer tube 35 so as to cause the jaws to converge, thereby closing the pouch. When the rod is pushed towards its distal end, the jaws bias laterally as described supra, allowing the mouth to prop up again.

Deployment and manipulation of the pouch 20 is also controlled by a toggle mechanism 50. The toggle mechanism 50 also serves as a means for decoupling the elongated jaws 41, 42 from the pouch 20. As noted supra, while engaged in the pouch, the jaws allow repeated partial opening and closing of the device so that a surgeon can collect a specimen at one site, partially close the jaws, move the pouch to another site, reopen the pouch, collect another specimen, and repeat these steps until all the required specimens are collected.

FIGS. 2a and 2b are exploded views of a preferred embodiment of the surgical device 10 for retrieving internal body tissue. The introducer tube 35 is used to insert a pusher rod 30 into a patient via a cannula. The pusher rod 30 is terminated by the two jaws (i.e. elongated spring-biased substrates) such that when fully deployed outside of the introducer, the jaws resemble two curved forks shaped as a partial circle. The collapsible pouch 20 is supported by equal length jaws 41, 42, so as to hang downwardly by the force of gravity.

The opening or mouth 25 of the pouch 20 is propped open by the laterally extended elongated jaws 41, 42. Specifically, the jaws are removably received by a collar or hem 27 defining the mouth 25 of the pouch 20. A perspective view of the pouch and jaws is found in FIG. 2b. The collar defines a channel 23 that circumscribes the mouth 25 of the pouch 20, with each end of the channel terminating with openings 29 positioned side by side and at a proximal region of the collar. The openings 29 provide a means for the elongated jaws to access the channel 23 and to slidably communicate with the pouch so as to define the shape of the mouth 25 of the pouch 20.

Intermediate the channel openings is a region of the pouch defining an aperture 28 adapted to removably receive the distal end 67 of the toggle 50.

Jaws Detail

The elongated jaws 41, 42 are formed of reversibly deformable material and, in their unconstrained state (i.e. their fully deployed uncompressed state), they form a loop 43, or a portion thereof, and such that the mouth 25 of the pouch 20 assumes the shape of the loop 43, with a gap 143 between the jaws. In an alternative embodiment, one elongated jaw forming substrate may be straight and the other one curved. The jaws may be of equal length (See FIG. 2b) or one may be longer than the other (See FIG. 2c). Each of the jaws can be chosen of variable lengths to shape the mouth 25 into the desired shape. For example, they can be compressed (i.e. reversibly deformed) to form two parallel linear members slidably received (with the jaws in their compressed state, i.e. in an undeployed configuration) by the distal end 31 of the introducer 35 for later deployment of the mouth 25 of the pouch 20 inside the patient. This is particularly advantageous as the invented device is delivered to the surgeon with the bag engaged by the pincers and deployed from the introducer tube. This allows the surgeon or the surgical suite personnel to pre-treat the bag prior to loading it into the distal end of the introducer tube.

Pincers of uneven length provide an appreciable amount of flexibility to left-handed or right-handed surgeons, allowing them to select the pincer configuration most convenient to them depending on the area where they are operating and special precautions that must be taken to avoid impacting neighboring organs.

FIG. 2c is a top view of the fork, toggle, and pusher rod assembly and FIG. 2d is a profile view of the fork, toggle, and pusher rod assembly taken along line 2d-2d of FIG. 2c.

Preferably, each of the elongated jaws 41, 42, have an oblong cross section 47, with the longer dimension of the cross section perpendicular to the plane p (phantom triangle depicted in dotted lines), as depicted in FIG. 2e. This feature limits bending of the jaws orthogonally to said plane when the jaws encounter resistance as the pouch collects a sample or when the filled pouch is weighed down by the tissue contained therein. The jaws have preformed curvatures which force the jaws 41, 42 into an expanded (i.e. relaxed) loop shape 43 when the jaws are extended or deployed from the distal end of the introducer 35. The jaws are flexible enough to be deformed into parallel rectilinear members that can be slid through the introducer 35

A rigid but light material such as Nickel Titanium alloy such as nitinol, a super-elastic alloy manufactured from nickel and titanium is especially suited for fabrication of the jaws. Other suitable materials are stainless steel and formed plastic. The jaws are manufactured from the selected material by forming the material in the required shape and heat-treating the material to fix that shape without further deformation.

As depicted in FIG. 2b, an embodiment of this invention features two jaws 41, 42 of unequal length, where, for example, a first jaw 41 is longer than a second jaw 42. It is envisioned that different combinations of jaws would be made available so that a surgeon may choose the combination best suited for the operation to be performed. With jaws of unequal length, the shape of any one jaw can be manipulated to increase the collection ability of the pouch by increasing the arc available from that pincer. This arrangement allows the surgeon to exert a force along a line nearly parallel to the introducer 35. The surgeon may attempt tissue removal at several sites along a line extending parallel to the pusher rod axis a. It can be appreciated that this aspect of the invention would facilitate scraping or avulsing of tissue adhering to a surrounding region.

Pouch Detail

This invention incorporates a pouch 20 bordered by a mouth 25 as depicted in FIG. 3. In general, Nylon or other plastics are suitable materials for fabrication of the pouch. In one embodiment, a two-layer configuration is used, one layer being a polyurethane laminate and the other rip-stop nylon.

A toggle 50, the function of which is described infra, is admitted through the aperture 28 described supra formed in a region of the collar of the pouch such that when the pouch is attached to the jaws the aperture is positioned in close spatial relationship to the distal end of the sleeve 35. The pouch further comprises a means for receiving a drawstring 89 such that the drawstring receiving means also serve as the jaw receiving means of the pouch, such means being the channel 23 formed by the collar 27. The drawstring traverses the channel 23 such that the ends of the string 89 protrude from the proximal end of the sleeve 35 so as to provide the surgeon a means for providing tension to the drawstring. This string facilitates closing of the mouth of the pouch after the jaws are retracted from the channel 23 formed in the hem 27 of the pouch, and prior to the tissue sample being retrieved from the surgical site.

FIG. 1a is a cross-sectional view of FIG. 1 along the line 1a-1a. It depicts the pusher rod 30 and two ends of the drawstring 89 as they are received in the introducer tube 35. In an alternative embodiment, one end of the string 89 is attached to the pouch hem at the orifice 28 and the other end of the string is threaded through the channel 23 so as to exit from the collar through the orifice 28 and be threaded through the introducer tube 35. In both embodiments, the open end of the drawstring 89 are received by the handle housing 72 (see FIG. 1).

In an exemplary embodiment, the fabric comprising the pouch is a rip-stop nylon cross-stitched polyamide 66 material with a polyurethane laminate, with thickness between 0.0035 and 0.0045 inches. This material has substantially higher puncture strength than other commonly used tissue pouch materials. For example, when a 5 mm diameter full radius rounded probe was used to simulate a 5 mm laparoscopic instrument, the puncture strength of the material was measured using a Chatilon 50 pound test device. A force in excess of 26 pounds was required to puncture the material.

The hem 27 of the pouch is radio-frequency welded to form the channel 23 which receives the jaws 41 and 42 so that the pouch depends from the jaws forming a continuous, homogeneous, perforation-free substrate with a stitch-free seam. This arrangement provides a tear-resistant construction that prevents the pouch from being accidentally ripped away from the jaws. The side 21 and bottom 22 of the pouch are also radio-frequency welded thus providing a totally impermeable pouch.

As shown in FIG. 8a, the invented device is delivered with the bag somewhat extended out of the introducer tube. The surgeon or the surgical suite personnel can pre-treat the bag with antibiotic, or saline solution, or some sort of solution that would optimize use of the bag in the body. For example, treating the bag with sterile saline solution dulls the surface of the bag making it less shiny so as to reduce glare by surgical lights also inserted within the body. Aside from the saline pretreatment, the bag can also be swabbed with antibiotic, or some sort of a marker that fluoresces when it contacts cancerous materials (or one may use fluorescent DNA tags where the DNA is complementary to whatever protein coat is associated with the target cancer tissue).

The fabric of the pouch can be selected to hang downwardly from the jaws, per the effect of gravity, as noted supra. Alternatively, the pouch comprises a stiffer material so as to retain its shape, volume and depth, no matter how it is positioned relative to gravity.

Toggle Structure and Function.

Another feature of the invention is a toggle and handle arrangement where the pusher rod handle must be in a predetermined alignment with the proximal end of the introducer handle in order to allow full protrusion, and therefore release, of the toggle from the introducer tube. This toggle/handle arrangement prevents accidental separation of the pouch from the jaws 41, 42. This full protrusion/handle arrangement also provides a movement of the toggle that is also controlled by a locking means for preventing rotation of the bag relative to the introducer tube. (See discussion infra related to FIGS. 7 and 8.)

Figure 4B:
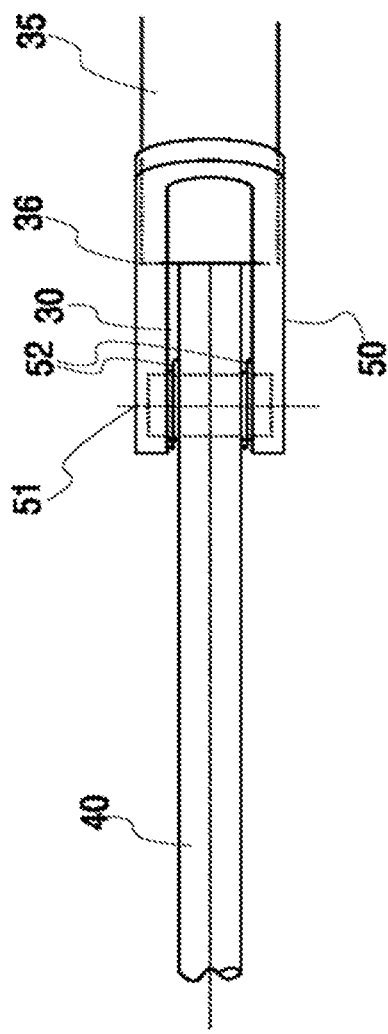
FIG. 4b is a detailed plan view of a toggle mechanism for a surgical device for retrieving internal body tissue, in accordance with features of the present invention.

Toggle mechanisms are depicted in FIGS. 4a through 4i. One embodiment of the toggle means is depicted in FIGS. 4a and 4b. It comprises a two-position post 50 that rotates about a pivot 51, such that the toggle post 50 swings through the arc "S" in the plane of the Figure, a plane orthogonal to the plane defined by the elongated substrates 41, 42 forming the hanger or jaws. The pivot 51 is situated intermediate the distal and proximal ends of the rod and in rotatable communication with the rod. FIG. 4i is a detail view of the toggle mechanism depicted in FIG. 4a with the toggle 50 entering the channel 23 through the aperture 28 and the jaws 41, 42 entering the channel 23 through the apertures 29.

FIGS. 4c and 4d are profile and top views of an alternative embodiment for the toggle 50. As shown in FIG. 4d, the toggle has a U-shape with the open end of the U pivoting around the pivot point 51. FIG. 4h is a detail view of the toggle mechanism depicted in FIG. 4c, in an alternative configuration to that depicted in FIG. 4i, with the toggle 50 and the jaws 41, 42 entering the channel 23 through the same aperture 28.

FIGS. 4e, 4f, and 4g depict yet another alternative embodiment for the toggle mechanism. The toggle mechanism is provided by a bendable metal or plastic curved member 49 that is either removably attached to or integrally molded to the distal end 31 of the pusher rod 30 (the member 49 may be in the shape of a loop or a tongue or may comprise one or more antennae). In FIG. 4e the member is depicted in a bent configuration after it has been threaded through the toggle-receiving aperture 28: in this configuration the toggle is bent half-a-circle and made to lie parallel to the pusher rod 30 as it is received in the introducer tube 35, with the tip 63 of the member pointing toward to the handle of the introducer. FIG. 4f depicts the situation when the pusher rod 30 has been pushed in the direction marked by the arrow I and the pouch is deployed so that the member 49 is in position 49b as it is about to disengage from the hem of the pouch. FIG. 4g depicts the situation when the rod is pulled back in the direction marked by the arrow J and the member 49 is in its relaxed position 49a and disengaged from the hem of the pouch. As noted supra, the toggle and jaws are both mounted in the rod such that the surgeon pulls the pusher rod and jaws into the introducer tube, the toggle slides completely out of the bag aperture 28 (FIG. 4g). Continued pulling of the rod causes the jaws 41, 42 to pull out of the channel 23 and through the introducer tube at the same time as the rod. In FIG. 4h the member 49 is depicted in a bent configuration so as to lie parallel and proximal to the jaws 41, 42 and constrained to be engaged in the aperture 28 in the channel 23 in the hem of the pouch. This embodiment has the advantage of comprising no external spring and no detachable parts.

As shown in FIG. 6a, when the device is assembled, a distal end 67 of the post 50 is inserted in the aperture 28 (optionally defined by a grommet) at the same time as the jaws 41, 42 are inserted in the channel 23 defined by the hem 27. This is designated the toggle "open" position (Depicted as "0" in FIG. 4a). The handle 71 of the pusher rod 30 is designed so that when it completely nests within the handle saddle 83 of the introducer 35, in a male/female configuration, the distal end of the rod emerges from the distal end of the introducer 35 to a distally biased position so as to allow the toggle free range of motion along a 180 degree arc such that the free end of the toggle extends away from the handle 71 and toward the pouch 20 (see discussion infra related to FIGS. 7c and 8a through 8d). In one embodiment of the invention, the toggle post 50 will not exit from the introducer tube until the handle 71 and the handle housing 72 are aligned in a complementary configuration depicted in FIG. 7a, the handle being provided with markings to serve as a visual cue to the surgeon that the device is now configured to detach the pouch from the pusher rod assembly (see discussion infra related to FIGS. 7c and 8e). When the handle and the handle housing are so positioned, the two interlock and the toggle 50 will exit from the distal end of the introducer and from the slit 28 and bias to a position intermediate the closed "C" and open "0" positions coming to rest against the distal end 31 of the pusher rod 30.

Toggle length is chosen to ensure that it cannot rotate through the aforementioned arc unless the pusher rod 30 it is fully extended (distally) from the introducer tube 35. While still constrained by the interior surfaces of the introducer tube, the toggle remains in an undeployed position and in frictional engagement with the interior surface of the introducer tube. This constraint serves as a means to prevent the jaw-forming elongated substrates 41, 42 from accidentally being retracted from the pouch hem, retreating into the introducer, and causing a premature detachment of the pouch from the pusher rod.

When the surgeon is ready to remove the pouch from the body (for example, after the pouch is loaded with tissue), the pusher rod 30 is fully extended distally so as to extend through the introducer tube and therefore clear the toggle from the confines of the interior surface of the introducer tube 35. At that point, the spring bias toggle flips to an intermediate retaining configuration, between positions "0" and "C" by still remaining protruding through the eyelet 28 formed on the proximal side of the pouch collar. A definitive tug away from the body cavity by the surgeon on the handle of the pusher rod causes the toggle post to engage the distal lip of the distal end of the introducer tube, thereby forcing the toggle to pivot about the pusher rod and toward the pouch such that the toggle end extends in a direction (designated as position "0") away from the surgeon.

This configuration, with the toggle pointing away from the surgeon, enables the toggle to slide out of (or otherwise disengage from) the eyelet 28 as the pusher rod 30 is pulled in a proximal direction to retract further yet out of the introducer. Concomitantly, the hanger 40 comprised of the jaws 41, 42, (heretofore described as attached to the distal end of the pusher rod 30), are pulled out of the channel 23 and retreat with the toggle post into the introducer. These actions leave the pouch 20 behind.

Once the pouch hanger 40 and pusher rod 30 are fully extracted from the introducer tube 35, the surgeon closes the pouch by pulling on ends of the drawstring 89. As noted supra, inasmuch as the drawstring resides in the channel 23 defined by the pouch hem, i.e., the same channel in which the jaws are positioned. Pulling on the drawstring protruding from the proximal positioned end 39 of the introducer tube 35 serves to constrict and ultimately close the pouch opening to assure containment of the tissue residing in the pouch during extrication of the pouch from the body. Further pulling of the pouch drawstring draws the closed pouch into the distal end of the cannula.

The spring-biased action of the toggle (from position "0" to position "C") disclosed above may be achieved by a helical spring 53 affixed to the pivot 51 and the post 50 (See FIGS. 2a through 2d) so as to cause the post 50 to spring back towards the introducer end 39 (i.e. towards the surgeon) once the post is released from the pouch hem 27. In still another embodiment, a torsion spring 52 may be affixed to the pivot 51 and the post 50 (See FIG. 4*b*) so as to cause the post 50 to spring back towards the introducer distal end 36. In another alternative embodiment of the toggle mechanism the toggle 50 constitutes a blunt end of a torsion spring 52 attached to the pusher rod 30.

In another embodiment, the toggle mechanism is actuated without the use of an external spring. As shown in FIG. 5*a*, the post 50 may be chosen to be of a diameter such that there is a frictional interaction between the pusher rod 30 assembly and the inside wall 37 of the introducer. Thus there is an outward, radially-directed pressure (i.e. a pressure applied in a direction perpendicular to and away from the longitudinal axis a of the introducer) on the introducer as the pusher rod and toggle are pushed through it. Elastic radial contraction of the introducer 35 when the toggle post 50 is released causes the toggle post to rotate proximally, (i.e., toward the proximal or surgeon end of the introducer (i.e. such that the post distal end 67 points away from the pouch hanger or fork 40 as indicated by the arrow T in FIG. 5*b*).

As the toggle post exits the introducer 35, there is a configuration depicted in FIG. 5*b* where the point 61, nearest to the pivot 51, has already exited from the introducer 35, while the diametrically opposite point 62 is still in the introducer where it experiences an inward radial force F due to the compression of the introducer 35. This unbalanced force F results in a clockwise torque about the pivot 51 and a consequent clockwise rotation of the post towards the end 36 of the introducer 35 as shown by the arrow T. This rotation is also facilitated by the drag on the device due to the surrounding body tissue, an effect that can be enhanced if the distal end 60 of the post 50 that exits from the hem 27 is cut at angle with respect to the length of the post. (See FIG. 5*c*). In this embodiment, the proximal end 60 of the toggle post 50 terminates in a plane that is at angle of roughly 45 degrees to the longitudinal axis a of the pusher rod 30 as the toggle comes to rest against the distal end 39 of the introducer. The toggle must be such that the distance between the pivot point 51 and the point 62 on the toggle distal end 67 is such that the toggle can reenter the introducer sleeve when the pusher rod is retracted.

Of course, one may combine two or more of the spring-back mechanisms suggested above.

In another alternative embodiment, the toggle is bent at a point 57 intermediate
the pivot point 51 and the distal end 67 projecting above the plane defined by the pouch hanger or pincer fork 40 (in the opposite direction of the pouch 20) (See FIG. 4*i*).

The toggle may be manufactured from steel, from the same material as the pincers, or from any other suitable material. Also, the toggle may be manufactured as part of the of the pusher rod mechanism, comprising a bent loop within the introducer tube that acts as a toggle.

FIGS. 6*a* through 6*d* illustrate in further detail the function of the toggle mechanism. FIG. 6*a* shows the toggle post 50 engaged with the pouch 20 wherein the distal end 67 is nested in the hem 27 through the aperture 28. It must be appreciated that the hem/aperture/toggle orientation is obtained by means of tension provided by the toggle post 50. As soon as the toggle post is withdrawn from the hem 27, and especially when the pouch is filled with a tissue specimen, the slit 28 is displaced with respect to the toggle post 50 and the pusher rod 30 (See FIG. 6*b*). FIG. 6*c* shows the toggle post at 90 degrees to the pusher rod 30. FIG. 6*d* shows the toggle post coming to rest against the introducer 35. When the final tissue sample has been collected the pusher rod 30 is retracted into the introducer 35, so that the above sequence is reversed from FIGS. 6*d* to 6*c* to 6*b*. At this juncture, one cannot reinsert the toggle post 50 into the slit 28 of the hem 27 because the post and the slit are now misaligned. Further retraction of the pusher rod 30 toward the surgeon brings the toggle post 50 against, but not inside, the hem 27 so that the toggle post now detaches the pouch from the pouch hanger or fork 40.

While the preceding discussion emphasized operation of the device with the toggle received in a channel 23 in the hem of the pouch through an orifice 28 when the device is first inserted in the patient, this is not necessary for effective operation of the device. The functions of the toggle can be equally well performed without the toggle having been inserted in the orifice 28 or with the toggle having been accidentally disengaged from the hem of the pouch before deployment of the device.

Handle Detail

FIGS. 7*a* and 7*b* are schematic front and back views of an exemplary embodiment of a handle assembly 70 that can be advantageously used with the invented device and FIGS. 8*a* through 8*f* illustrate the use of this handle assembly. The handle assembly comprises a handle 71 that is rigidly attached to the pusher rod 30 and a housing 72 that is rigidly attached to the introducer tube 35, so as to render the housing 72 in rotatable communication with the handle 71 through a bore 73 traversing the housing. The housing 72 also comprises a groove 79 adapted to receive a portion 78 of the handle 71 in a male-female configuration. The assembly 70 has a front face depicted in FIG. 7*a* comprising a first surface 76 of the handle 71 defining a protrusion 75 aligned with the axis a of the pusher rod 30. A first surface 80 of the housing 72 comprises a slot 83 or saddle adapted to slidably receive the protrusion 75. The first surface 80 of the housing 72 further comprises a slit 74 adapted to frictionally receive the ends of the drawstring 89. Also, the first surface 76 of the handle 71 comprises a marking 91, such as the word "UP" to distinguish it from the back face of the handle depicted in FIG. 7*b*. Stripes 121 on the first surface of the housing come into alignment with stripes 122 on the protrusion when the handle is fully inserted and this serves as a visual indicator to the surgeon that the handle is fully inserted indeed.

FIG. 7*b* depicts the back face of the handle assembly, showing that the second surface 82 of the housing 72 comprises a marking 99 such as a semi-circular arrow 99 together with a directive such as "TO UNLOAD".

FIG. 7*c* depicts the orientation of the handle assembly when the device is inserted in the patient. The surgeon inserts the device with the first surface 76 of the handle 71 coplanar to the second surface 82 of the housing 72 so that the protrusion 75 abuts the proximal edge 84 of the housing 72 and the pusher rod 30 is prevented from fully exiting the introducer tube 35.

Operation of the Device

FIGS. 8*a* through 8*f* illustrate the operation of the device. In FIGS. 8*a* through 8*d* the first surface 76 of the handle 71 is facing in the same direction as the second surface 82 of the housing 72 so that the protrusion 75 abuts the proximal edge 84 of the housing (See FIG. 7*c*). In FIG. 8*a* the pouch 20 is shown extending from the distal end of the introducer tube 35. This allows for pretreatment. In FIG. 8*b* the pouch is shown being withdrawn into the introducer tube 35. Throughout this sequence the arrow 95 indicates the direction in which the handle 71 is moved. In FIG. 8*c* the device is introduced through a trocar port 93 connected to a patient. The surgeon places the pouch into position, pushes the handle towards the housing and the pouch deploys automatically when the handle 71 comes into contact with the housing 72 so that the protrusion 75 abuts the housing 72

(see FIG. 7c). FIG. 8d depicts the surgeon placing a tissue sample 96 into the pouch. Then the surgeon rotates the housing 180 degrees as directed by the semi-circular arrow 99 while keeping the handle immobile in the "up" position. In FIG. 8e the surgeon inserts the protrusion 75 into the slot 83 so as to cause the rod to extend to its distal-most position. (See FIG. 8e2 showing the protrusion 75 fully received in the slot 83 with the stripes 121 on the housing brought into alignment with the stripes 122 on the protrusion.) Finally, the surgeon pulls the handle 72, pusher rod 30, and pouch hanger or fork assembly 40 from the pouch and the introducer tube 35 as shown in the detail FIG. 8e1.

In FIG. 8f the mouth of the pouch is closed by pulling on the draw string and then the surgeon removes the introducer tube 35 and the trocar 93 outside the patient and brings the mouth of the pouch to outside the abdomen. The tissue is removed from the pouch and then the pouch is removed from inside the patient.

Outside the Patient (Proximal) Portion of the Device

The proximal end of the device is designed so as to aid the surgeon in ascertaining the position and functioning of the distal end of the device. In one embodiment, the plane defined by the fully deployed hanger 40 (comprised of the elongated substrates) is fixed in relation to the handle 71 orientation. This requires the elongated substrates 41, 42, to be rigidly attached to the distal end of the pusher rod 30, so as not to be in rotatable communication with the rod. As such, the handle 71, pusher rod 30, and hanger 40 move as a single unit when the rod is rotated, and/or slid in and out of the introducer tube 35. FIGS. 7a and 7b depict means to indicate to the surgeon the orientation of the pouch.

The introducer tube 35 comprises at its proximal end 39 a handle housing 72 adapted to receive a handle 71 in two different configurations.

FIG. 7c depicts the orientation of the handle assembly when the device is inserted in the patient. The surgeon inserts the device with the front face 76 of the handle 71 facing in the same direction as the back face 82 of the housing 72 so that the protrusion 75 abuts the proximal edge 84 of the housing 72.

When the handle 71 is fully inserted in the housing 72 (FIGS. 7a and 7b) the pusher rod 30 and the introducer 35 are locked relative to each other, such that one is not rotating about or within the other. It is in this fully nested position that the toggle emerges from the distal end of the introducer tube, is released from the pouch 20, and springs back to its "closed" or "C" position. Pulling of the pusher rod in a proximal direction (i.e., toward the surgeon or operator of the device) causes the toggle arm to engage with the distal lip or periphery of the introducer tube, thereby forcing the toggle to reset to a pouch-releasing configuration (position "0") as proximally directed force on the pusher rod is maintained.

The toggle also facilitates loading of the device by acting on the pouch and pulling it into the introducer tube. The device is loaded by the scrub nurse or assistant and delivered to the surgeon in a loaded condition with the pusher and toggle positioned in the bag aperture 28 and also in the introducer tube. The surgeon or an attendant now pulls on the handle of the introducer and pulls the pusher, the toggle, and the pouch into the introducer tube. The tight fit between the pusher handle and the introducer handle prevents accidental unloading of the toggle from the distal end of the introducer tube. The toggle not only facilitates deployment of the pouch but allows loading of the pouch into the introducer tube without using long tails to push the pouch or complicated structures to which the pouch is attached.

Alternative Embodiment

Figure 9:
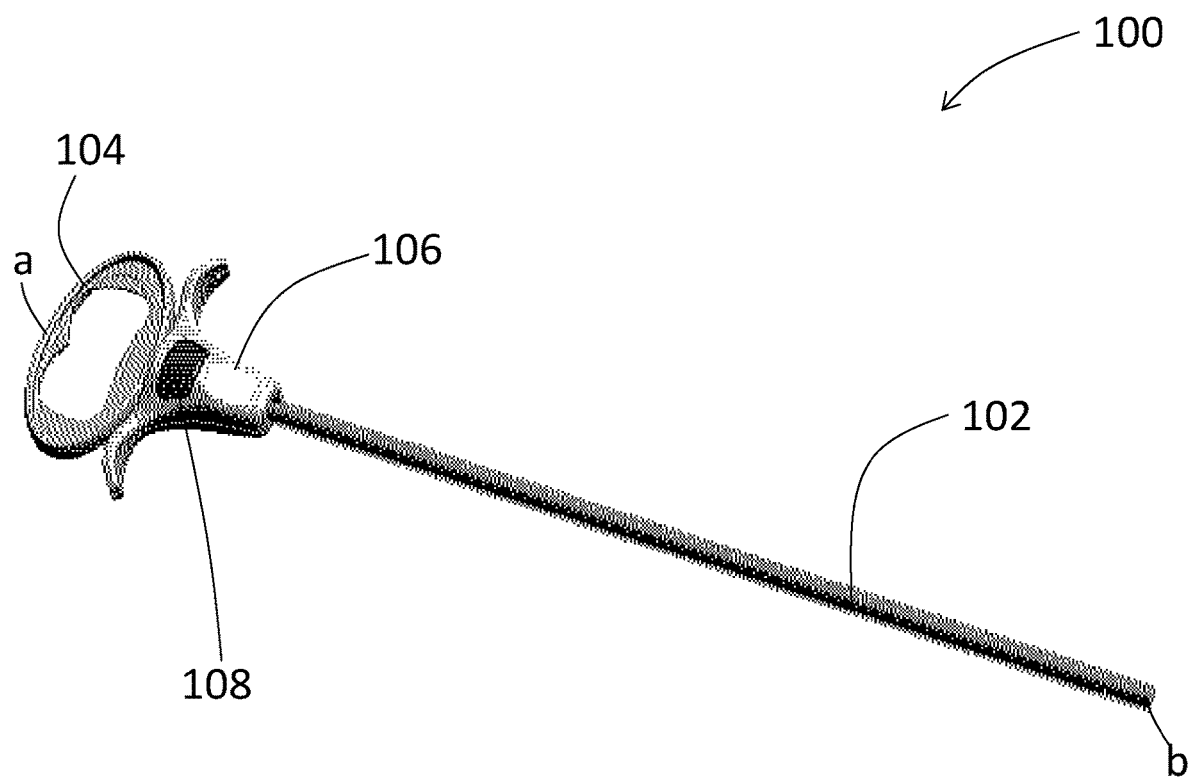
FIG. 9 is a view of an introducer assembly for an additional embodiment of the invention.

Turning now to FIG. 9, depicted therein is an alternative embodiment 100 of the tissue retrieval device introducer tube assembly. The depicted embodiment is designed for use with a smaller opening within the patient's body. In the depicted embodiment, the tissue retrieval device can be used with an opening having a diameter of 8 mm. Such openings are generally used by instruments used in robotic surgery.

The smaller embodiment 100 consists of the same overall components, including an introducer tube 102, a handle assembly 104, and handle housing 106. The rod with arms to support a tissue retrieval pouch extends from the handle assembly 104. In the embodiment 100 depicted in FIG. 9, the rod with arms is stowed in the introducer tube 102. The handle housing 106 includes a push button 108 which releases the tissue retrieval pouch from the arms.

In this way, the introducer tube, while having a smaller diameter, remains approximately the same length as for embodiments used with larger incisions. In one embodiment, the length of the embodiment 100 from point a to point b shown in FIG. 9, is approximately 13½ inches.

Figure 10:
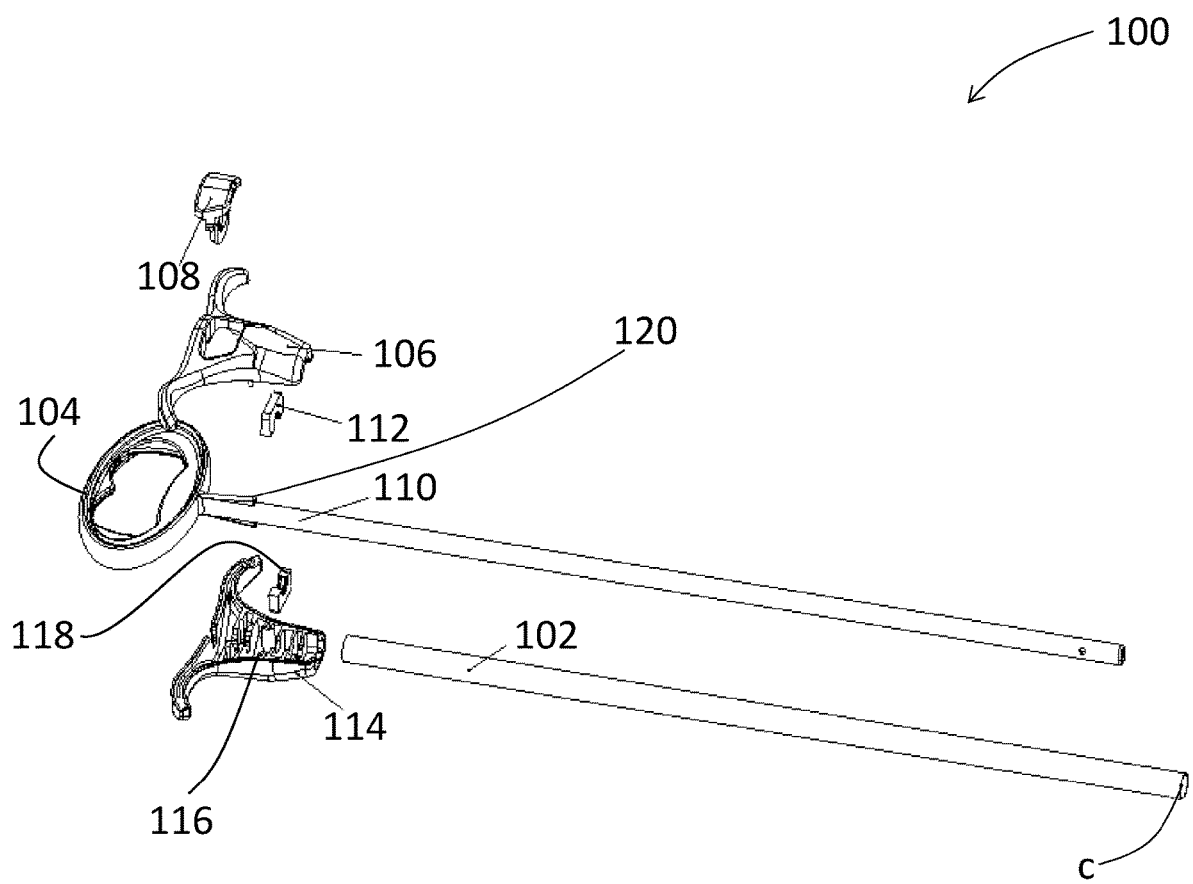
FIG. 10 is an exploded view of an embodiment of the invention.

Turning to FIG. 10, depicted therein is an expanded view of the embodiment 100, showing the components of the embodiment in a disassembled state. The introducer tube 102 is manufactured separately from the handle housing 106 and is received by the handle housing 106 and handle housing secondary component 114. The secondary component 114 includes a channel 116 which receives a lower seal 118. The lower seal 118 and upper seal 112 engage the interior components of the device, such as the rod 110. The lower seal 118 and upper seal 112 fluid communication between the handle portion of the rod with the lower portion of the rod 110. The seals 118, 120 also accommodate a draw string (not shown). The push button 108, upon actuation, allows for the rod to be shifted in position and to allow the rod to extend beyond the edge c of the introducer tube and therefore release the pouch, as shown in earlier figures.

In the depicted embodiment, the radius of the introducer tube is 0.167 inches. The radius of the rod is 0.152 inches.

Figure 11A:
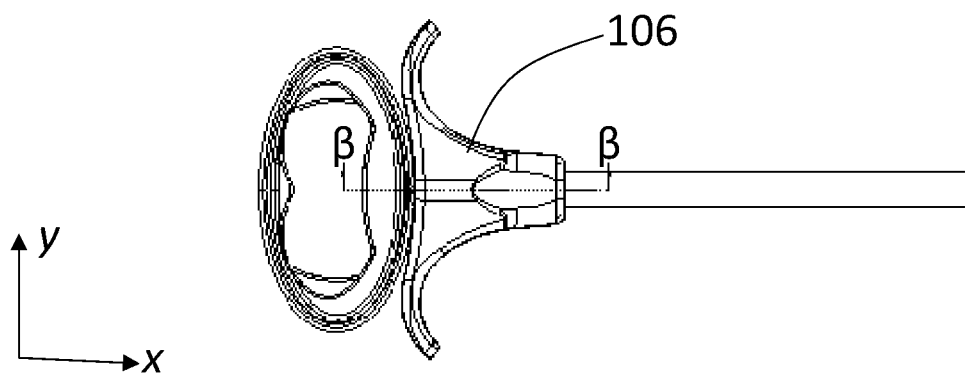
FIGS. 11A and 11B are detailed views of one embodiment of the invention.
Figure 11B:
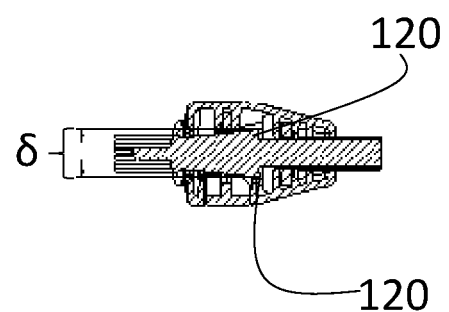

As shown in FIGS. 11A and B, the handle assembly 106 is substantially symmetrical along the y axis shown in FIG. 11A. The cut-away view along the line p is shown in FIG. 11B.

The distance 6 between the sides of the protrusions 120 is 0.457 inches. The small distances and small components allow the device to be compatible with small openings in patient bodies. In one embodiment, the inner diameter is 0.315 inches (8.01 mm) and the outer diameter of the introducer is 0.345 inches (8.76 mm).

Despite the introducer tube being compatible with small openings, a tissue retrieval bag with a capacity of 125 mL can still be accommodated within the introducer tube. The tissue retrieval bag is folded and wrapped around the rod, in one embodiment.

While the depicted embodiment is compatible with 8 mm openings generally used in robotic surgery, the depicted tool actuation is designed for manual operation by a hand, either a human or artificial hand. The same finger openings and push button are defined as in earlier embodiments. In another embodiment (not shown), the handle area is replaced with an instrument tool attachment substrate to allow the tissue retrieval embodiment to be coupled to the wrist of a surgical robot.

While the invention has been described in the foregoing with reference to details of the illustrated embodiment, these details are not intended to limit the scope of the invention as defined in the appended claims.

The invention claimed is:

1. A method of retrieving tissue from a patient using an instrument comprising:
   a) inserting the instrument through a cannula in a patient;
   b) opening a pouch of said instrument;
   c) positioning said pouch at a first site within the patient;
   d) retrieving tissue from said first site;
   e) closing the pouch;
   f) positioning said pouch to another site within the patient;
   g) reopening said pouch;
   h) retrieving tissue from said another site;
   i) repeating steps e-h for any remaining sites within the patient;
   wherein said instrument comprises a sleeve defining a proximal end and a distal end, said distal end adapted for insertion in the cannula; a rod in slidable communication with said sleeve, said rod having a distal end supporting a u-shaped toggle and laterally biased jaws and a proximal end comprising a handle to manipulate the rod; and a pouch in slidable communication with the jaws and the u-shaped toggle wherein said jaws and the u-shaped toggle combined are a means for deployment and control of repeated opening and closing of said pouch.

2. The method of claim 1 wherein said u-shaped toggle comprises a two-position post.

3. The method of claim 1 wherein said u-shaped toggle comprises a bendable member.

4. The method of claim 3 wherein said bendable member comprises a plastic bendable member.

5. The method of claim 3 wherein said bendable member comprises a metal bendable member.

* * * * *